United States Patent
Endou et al.

(10) Patent No.: US 7,595,423 B2
(45) Date of Patent: Sep. 29, 2009

(54) PROCESS FOR PRODUCING TRANS-1,4-CYCLOHEXANEDICARBOXYLIC ACID

(75) Inventors: Koetsu Endou, Yokohama (JP); Hirofumi Nakamura, Kurashiki (JP); Shinichi Tanaka, Kurashiki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/924,161

(22) Filed: Oct. 25, 2007

(65) Prior Publication Data

US 2008/0051600 A1 Feb. 28, 2008

Related U.S. Application Data

(63) Continuation of application No. 10/831,156, filed on Apr. 26, 2004, which is a continuation of application No. PCT/JP02/11058, filed on Oct. 24, 2002.

(30) Foreign Application Priority Data

| Oct. 26, 2001 | (JP) | 2001-329101 |
| Dec. 4, 2001 | (JP) | 2001-369959 |
| Apr. 16, 2002 | (JP) | 2002-113047 |
| May 23, 2002 | (JP) | 2002-149302 |

(51) Int. Cl.
*C07C 61/00* (2006.01)

(52) U.S. Cl. .................................................. 562/509

(58) Field of Classification Search .................. 562/509
See application file for complete search history.

(56) References Cited

U.S. PATENT DOCUMENTS

| 2,888,484 A | 5/1959 | Dehm et al. |
| 3,326,972 A | 6/1967 | Schenk et al. |
| 5,430,184 A | 7/1995 | Tateno et al. |

FOREIGN PATENT DOCUMENTS

| JP | 39-27244 | 11/1964 |
| JP | 45-39697 | 12/1970 |
| JP | 49-81349 | 8/1974 |
| JP | 49-82648 | 8/1974 |
| JP | 50-10581 | 4/1975 |
| JP | 58-24540 | 2/1983 |
| JP | 58-194839 | 11/1983 |
| JP | 58-198439 | 11/1983 |
| JP | 6-184041 | 7/1994 |
| JP | 2000-198760 | 7/2000 |
| JP | 2002-363126 | 12/2002 |

OTHER PUBLICATIONS

Patent Abstracts of Japan, JP-58-024540, Feb. 14, 1983.

*Primary Examiner*—Taylor Victor Oh
(74) *Attorney, Agent, or Firm*—Oblon, Spivak, McClelland, Maier & Neustadt, L.L.P.

(57) ABSTRACT

A subject for the invention is to obtain trans-1,4-cyclohexanedicarboxylic acid (t-CHDA) in a high concentration by efficiently isomerizing cis-1,4-cyclohexanedicarboxylic acid (c-CHDA) by a simple method. The invention provides: (1) a process for producing t-CHDA which comprises heating crude CHDA to 180° C. or higher in an inert atmosphere and causing the t-CHDA formed by isomerization to precipitate in the molten c-CHDA while holding the crude CHDA at a temperature in the range of not lower than 180° C. and less than the melting point of t-CHDA; (2) a process for producing t-CHDA, wherein crude CHDA which is powdery or granular is heat-treated at a temperature of not lower than the melting point of c-CHDA and lower than the melting point of t-CHDA to thereby isomerize the cis isomer to the trans isomer while maintaining the powdery or granular state; (3) a process for producing t-CHDA, wherein crude CHDA is held at a temperature of not lower than the melting point of c-CHDA and lower than the melting point of t-CHDA in an inert atmosphere while maintaining flowing to thereby obtain powdery or granular t-CHDA; and (4) a process for purifying crude CHDA in which crude CHDA obtained through the step of hydrogenating TPA or the like is heated in an atmosphere of an inert gas to volatilize and remove impurities.

8 Claims, No Drawings

PROCESS FOR PRODUCING TRANS-1,4-CYCLOHEXANEDICARBOXYLIC ACID

FIELD OF THE INVENTION

The present invention relates to a process for producing trans-1,4-cyclohexanedicarboxylic acid (hereinafter referred to as t-CHDA) by heating cis-1,4-cyclohexanedicarboxylic acid (hereinafter referred to as c-CHDA) to obtain t-CHDA, which is isomeric with c-CHDA. The invention further relates to novel t-CHDA of high quality.

BACKGROUND ART

CHDA is useful as a starting material for medicines, synthetic resins, synthetic fibers, dyes, and the like. In particular, t-CHDA is useful as a starting material in producing resins and fibers excellent in heat resistance, weatherability, physical strength, etc. There is a desire for CHDA having a high t-CHDA concentration.

A method generally employed for producing CHDA is to hydrogenate the benzene ring of a TPA derivative. For example, use is being made of a method which comprises converting the carboxyl groups of TPA into a metal salt, e.g., sodium salt, or into any of various esters before hydrogenating the benzene ring (nucleus hydrogenation) and a method in which TPA having the carboxyl groups is subjected to nucleus hydrogenation.

(1) Processes for CHDA Production

Known processes for producing CHDA through the step of hydrogenating not a TPA derivative but TPA include the following.

(i) A process comprising hydrogenating TPA in a solvent for TPA at 150 to 300° C. and at least 1,000 p.s.i.g. using a palladium catalyst to obtain crude CHDA, dissolving the crude CHDA in an aqueous alkali solution, and then conducting precipitation with an acid to purify (see patent document 1).

(ii) A process comprising hydrogenating TPA under the conditions of 150° C. and 100 kG in the presence of palladium or ruthenium, filtering the resultant liquid reaction mixture under specific temperature conditions, and crystallizing a CHDA from the filtrate (see patent document 2).

(iii) A process comprising hydrogenating TPA in a glass autoclave at 130° C. and a hydrogen pressure of from 8.3 to 9.8 kg/cm$^2$ in a water solvent in the presence of palladium and subjecting the liquid reaction mixture to steam distillation to purify (see patent document 3).

The CHDA obtained by those production processes have had a low purity. In the process (i) in which purification is conducted by precipitation with an acid, inclusion of inorganic salts derived from sodium hydroxide, hydrochloric acid, and the like is unavoidable. In the process (ii) involving crystallization, inclusion of TPA, which is used as the starting material, and of by-products including trans-4-methylcyclohexanecarboxylic acid (hereinafter referred to as "t-MCHA"), cis-4-methylcyclohexanecarboxylic acid (hereinafter referred to as "c-MCHA"), and cyclohexanecarboxylic acid (hereinafter referred to as "CHA") occurs. Because of these, it has been impossible to obtain a high-purity CHDA by either of these processes (i) and (ii). The process (iii) involving steam distillation requires a large amount of steam and necessitates wastewater treatment facilities. The process (iii) hence has had a problem concerning profitability.

Furthermore, in those processes, the hydrogenation of the benzene ring of TPA yields isomers and, hence, the CHDA obtained is a mixture of c-CHDA (melting point, 170-171° C.) and t-CHDA (melting point, 312-313° C.). The concentration of t-CHDA, which is the target compound, is as low as about from 20 to 50%, although it depends on reaction conditions. Consequently, techniques for improving the concentration of t-CHDA after CHDA are obtained from TPA are being investigated. A known technique for heightening the concentration of t-CHDA is to heat c-CHDA and thereby isomerize it into t-CHDA.

(2) Thermal Isomerization of CHDA (i) A method is known in which c-CHDA is heated to 250° C. or higher, preferably to the melting temperature of t-CHDA (310-313° C.) or a higher temperature, to obtain t-CHDA (see patent document 4). In an Example of patent document 4, there is a statement to the effect that t-CHDA of 98% was obtained by a method comprising heating a mixture of c-CHDA and t-CHDA to 310-320° C., holding it for 5 minutes, subsequently cooling the resultant homogeneous melt to ordinary temperature, and recrystallizing the reaction product from water using activated carbon.

This method described in patent document 4 is unclear with respect to the concentration of t-CHDA after the heating and before the recrystallization. The heating of the reactant is presumed to be conducted in air because the Example contains no particular statement concerning an atmosphere for reactant heating. It is hence thought that the CHDA is oxidized to generate impurities. Furthermore, since the mixture is heated to a temperature not lower than the melting point of the t-isomer, the t-CHDA obtained is exceedingly hard and is difficult to handle. In addition, t-CHDA having a high purity of 98% can be finally obtained only when t-CHDA is recrystallized from water using activated carbon after the heat treatment.

Namely, the method described in patent document 4 necessitates a two-stage operation, which is complicated. The present inventors followed up the method described in patent document 4. As a result, it was found that when the mixture which has been heat-treated at a temperature not lower than the melting point of t-CHDA is cooled to room temperature, the CHDA obtained is exceedingly hard and are difficult to handle and the concentration of the t-CHDA obtained through an isomerization reaction is low. Furthermore, the reactor was highly corrodible.

Known as a technique for improving handleability is (ii) a method which comprises heating and isomerizing c-CHDA at a temperature of 250° C. or higher to obtain t-CHDA, mixing the t-CHDA with an inert liquid substance to prepare a suspension, and obtaining the t-CHDA therefrom (see patent document 5). In an Example of patent document 5, a procedure is described which comprises keeping c-CHDA molten at 300° C. in a nitrogen atmosphere for 30 minutes, subsequently adding a liquid paraffin thereto, cooling the mixture to room temperature, and separating the resultant slurry, followed by washing with butanol and water to obtain t-CHDA having a purity of 99.5%.

In the method described in patent document 5, it is necessary to elevate the temperature of the reaction system to the melting temperature or higher and to disperse the melt with a liquid paraffin. It is also necessary to conduct washing with butanol and water in order to remove the liquid paraffin from the t-CHDA dispersed. In addition, it is thought that to completely remove the liquid paraffin by the washing is difficult.

(3) Thermal Isomerization of Aqueous CHDA Solution

A method is known which comprises heating an aqueous solution of c-CHDA to 240° C. or higher under pressure to thereby obtain t-CHDA (see patent document 6). In an Example of patent document 6, there is a statement to the effect that t-CHDA was obtained in a yield of 58.9% by heating an aqueous solution of c-CHDA at 245 to 250° C. in a nitrogen atmosphere for 2 hours, cooling the solution, subsequently filtering the resultant slurry at 70° C., and cleaning the solid with hot water.

In the method described in patent document 6, c-CHDA is isomerized into t-CHDA in an aqueous solution. However, this reaction in an aqueous solution is effective only in heightening the proportion of t-CHDA to about 60%, and about 40% of the c-CHDA remains without being isomerized.

(4) Thermal Isomerization with Alkali Metal Salt

A method is known in which an alkali (alkaline earth) metal salt of a c/t-CHDA mixture is heated in a solid phase in the presence of an alkali metal hydroxide or alkaline earth metal hydroxide to obtain t-CHDA (see patent document 7). In an Example of patent document 7, a procedure is described which comprises concentrating a mixture of c-CHDA, sodium hydroxide, and water to dryness under reduced pressure, heating the resultant solid at 200° C. in a sealed tube for 1 hour, cooling the resultant mixture, subsequently dissolving it in water, and then subjecting the solution to acid precipitation with hydrochloric acid to obtain t-CHDA in a yield of 95%.

In the method described in patent document 7, the alkali (alkaline earth) metal salt is subjected to an isomerization reaction in the presence of an alkali metal hydroxide or alkaline earth metal hydroxide. It is therefore necessary that after completion of the reaction, the reaction product should be dissolved and converted to the carboxylic acid through precipitation with an acid. Furthermore, it is presumed that in this method, the alkali (alkaline earth) metal comes as an impurity into the reaction product.

[Patent Document 1]
U.S. Pat. No. 2,888,484

[Patent Document 2]
JP-A-58-198439

[Patent Document 3]
JP-A-6-184041

[Patent Document 4]
JP-B-39-27244

[Patent Document 5]
JP-A-49-81349

[Patent Document 6]
JP-A-49-82648

[Patent Document 7]
JP-A-58-24540

As described above, the related-art techniques in which c-CHDA is isomerized into t-CHDA necessitate a complicated operation. Furthermore, in the case of obtaining the target compound by mere heating by a simple method, difficulties have been encountered in handling the CHDA's resulting from the isomerization reaction. There has hence been a desire for a method for obtaining t-CHDA in a high concentration from c-CHDA with high productivity.

In addition, in the related-art techniques for obtaining t-CHDA, a TPA derivative which can be easily hydrogenated industrially has been used as a starting-material TPA for obtaining crude CHDA therefrom. Namely, when a metal salt of TPA is used as a starting-material TPA, the metal, e.g., sodium, remains. When a TPA ester is used, the ester is first converted into a salt and then subjected to precipitation with an acid. Because of these, polymers obtained from this t-CHDA have had the following problems: (1) they contain metallic impurities derived from the metal salt of TPA; (2) a component of the acid used for the acid precipitation, e.g., chlorine or sulfur, remains; (3) the residual acid component corrodes apparatus and others; and (4) the polymers have a low value of transmittance at 340 nm, which property is an index to the degree of coloring. High-quality t-CHDA has been desired.

DISCLOSURE OF THE INVENTION

The present inventors made intensive investigations in order to develop a simple method for obtaining t-CHDA in a high concentration by efficiently isomerizing c-CHDA. As a result, they have found that t-CHDA having a high concentration is efficiently obtained when a reaction system is held at a temperature in a given range. The invention has been thus completed.

The inventors have further found that when CHDA in which the proportion of the trans isomer to the CHDA (hereinafter referred to as t/(c+t)), is 0.5 or higher is used as a reactant material to conduct thermal isomerization at a temperature lower than the melting point of t-CHDA, then the CHDA retains the shape of the starting material for isomerization reaction throughout the isomerization reaction. As a result, the CHDA obtained is in a powdery or granular state and, hence, they neither adhere to the wall of the reactor nor form a hard mass. The resultant CHDA can hence be easily taken out of the reactor. Namely, the inventors have found that this method is an excellent industrial process. The invention has been thus achieved.

The inventors have still further found that when a mixture of c-CHDA and t-CHDA is thermally isomerized by holding the mixture at a temperature of from the melting point of c-CHDA to below the melting point of t-CHDA while causing the mixture to flow, then powdery or granular CHDA having a t-CHDA content of 85% or higher is obtained from the mixture, which retains the solid-phase state or undergoes a molten state. The invention has been thus completed.

The inventors made intensive investigations in order to develop a method for obtaining a high-purity CHDA. As a result, they have found that the impurities contained in crude CHDA obtained through the step of hydrogenating TPA, an alkali metal salt of TPA, or a TPA ester (hereinafter, these are inclusively referred to as "TPA or the like") can be volatilized and removed by heating the crude CHDA in an atmosphere of an inert gas. The invention has been thus completed.

Furthermore, the inventors have found that when crude CHDA obtained by the nucleus hydrogenation of TPA, which is not in ordinary industrial use, is used to thermally isomerize the c/t-CHDA mixture under specific conditions, then high-quality t-CHDA which has been unobtainable so far can be provided. The invention has been thus completed.

Namely, an essential point of the invention resides in a process for producing t-CHDA, characterized by heating crude CHDA to the melting point of c-CHDA or a higher temperature in an inert atmosphere and causing t-CHDA to precipitate in the molten c-CHDA while holding the crude CHDA at a temperature in the range of not lower than the melting point of c-CHDA and lower than the melting point of t-CHDA.

Another essential point of the invention resides in a process for producing t-CHDA, characterized in that crude CHDA which is powdery or granular is heat-treated at a temperature of not lower than the melting point of c-CHDA and lower than the melting point of t-CHDA in an inert atmosphere to thereby isomerize the cis isomer to the trans isomer while maintaining the powdery or granular state.

A still other essential point of the invention resides in a process for producing t-CHDA, characterized in that crude CHDA is held at a temperature of not lower than the melting point of c-CHDA and lower than the melting point of t-CHDA in an inert atmosphere while maintaining flowing to thereby obtain powdery or granular t-CHDA.

The invention furthermore provides t-CHDA satisfying the following (a) and (b) (hereinafter referred to as "high-quality t-CHDA"):
(a) a t-isomer content is 90% or higher; and
(b) a transmittance at 340 nm is 85% or higher in an aqueous alkali solution.

BEST MODE FOR CARRYING OUT THE INVENTION

The contents of the invention will be explained below in detail.

<Crude CHDA>

<Processes for Producing Crude CHDA>

Processes for producing crude CHDA are not particularly limited, and CHDA produced by a known method can be used. For example, crude CHDA obtained by hydrogenating the benzene ring of either TPA or a derivative thereof can be advantageously used.

The nucleus hydrogenation of TPA or a derivative thereof gives an aqueous solution of crude CHDA which includes a mixture of the trans isomer and the cis isomer and in which t/(c+t) is generally from 0.2 to 0.5. Furthermore, crude CHDA recovered from the liquid reaction mixture obtained by the nucleus hydrogenation of TPA or a derivative thereof or crude CHDA contained in the residue resulting from t-isomer recovery from the liquid reaction mixture can be used as a starting material.

The benzene ring of either TPA or a derivative thereof may be hydrogenated in the following manner as described in, e.g., JP-A-58-198439. TPA, an alkyl ester thereof, or a salt thereof with a metal, e.g., an alkali metal, is subjected to nucleus hydrogenation in a liquid phase in the presence of a solvent, hydrogen, and a hydrogenation catalyst. In the case where an alkyl ester or metal salt of TPA is used as a reactant material, the resultant reaction product can be used as a starting material for isomerization after having been returned to the carboxylic acid form. However, it is preferred to use TPA from the standpoint of the possibility of impurity inclusion.

For obtaining the high-quality t-CHDA according to the invention which is reduced in the content of specific impurities, crude CHDA obtained by the nucleus hydrogenation of TPA is used.

<Process for Producing Crude CHDA for Obtaining High-Quality t-CHDA of the Invention>

The hydrogenation reaction of TPA for obtaining the high-quality t-CHDA of the invention may be conducted by a known method. A preferred reaction solvent is one which volatilizes at the temperature to be used for the isomerization reaction of crude CHDA. Examples of such solvents include water; carboxylic acids such as acetic acid and propionic acid; cyclic ethers such as 1,4-dioxane; alcohols such as methanol and ethanol; glymes such as monoglyme and diglyme; and the like. Preferred of these is water.

As the hydrogenation catalyst is generally used a noble-metal catalyst such as ruthenium, palladium, or platinum. These catalysts preferably are used after having been deposited on a carbonaceous support such as graphite or activated carbon, a metal oxide support such as alumina, silica, zirconia, or titania, or the like. It is especially preferred to use the catalyst deposited on activated carbon.

The hydrogen pressure in the hydrogenation reaction is generally from 0.2 to 30 MPa. It is preferably from 0.5 to 20 MPa, especially from 1 to 17 MPa.

The reaction temperature is preferably from 50 to 200° C., especially from 70 to 170° C.

The hydrogenation reaction can be conducted by any of batch, semi-continuous, continuous, and other processes.

After completion of the hydrogenation reaction, the catalyst is removed by solid/liquid separation. Subsequently, the solvent is removed from the liquid obtained, or crude CHDA is crystallized from the liquid. Thus, crude CHDA is obtained.

<Proportion of c-CHDA to t-CHDA>

The proportion of c-CHDA to t-CHDA in the crude CHDA is not particularly limited. However, the proportion of t-CHDA to the CHDA is generally 1% by weight or higher, preferably 20% by weight or higher. From the standpoint of production efficiency, t/(c+t) is generally 80% by weight or lower.

It is not particularly limited because it exerts a limited influence on the results of isomerization reaction. According to the process of the invention, the isomerization can be carried out irrespective of the proportion. Consequently, even when crude CHDA having a high t-CHDA concentration is used, an even higher concentration can be obtained.

It is noted that c-CHDA melts in an initial stage in isomerization reaction. In the case where the proportion of c-CHDA is high, the crude CHDA comes into a slurry or solution state in an initial stage in the reaction, before the isomerization reaction proceeds and t-CHDA begins to precipitate. In the case where the proportion of c-CHDA is low, isomerization proceeds while enabling the crude CHDA to apparently retain a solid-phase state.

<Proportion of c-CHDA to t-CHDA for Maintaining Powdery or Granular State>

One feature of the invention resides in that crude CHDA which are powdery or granular are heat-treated at a temperature of from the melting point of c-CHDA to below the melting point of t-CHDA to thereby isomerize the cis isomer to the trans isomer while maintaining the powdery or granular state. In order to maintain the powdery or granular state of the crude CHDA at a temperature of from the melting point of c-CHDA to below the melting point of t-CHDA, the value of t/(c+t) in the reactant material is regulated. The larger the value of t/(c+t) is, the easier the maintenance of the powdery or granular state is. Because of this, powdery or granular crude CHDA is used in which t/(c+t) is generally 0.5 or larger, preferably 0.55 or larger, more preferably 0.60 or larger.

Since the isomerization temperature is not lower than the melting point of c-CHDA, the c-CHDA melts under the isomerization conditions. The surface of the powdery or granular material in this case hence comes into a partly dissolve state. However, the powdery or granular material as a whole retains a solid-phase state.

<Processes for Producing Crude CHDA in which t/(c+t) is 0.5 or Higher>

Examples of methods for obtaining powdery or granular crude CHDA in which t/(c+t) is 0.5 or higher from crude CHDA comprising a mixture of the trans isomer and the cis isomer include: a method which comprises adding t-CHDA to the crude CHDA comprising a mixture of the trans isomer and the cis isomer; a method in which t-CHDA is separated by crystallization from an aqueous solution of the crude CHDA comprising a mixture of the trans isomer and the cis isomer; a method in which an aqueous solution of the crude CHDA comprising a mixture of the trans isomer and the cis isomer is heat-treated to conduct isomerization; a method in which the crude CHDA comprising a mixture of the trans isomer and the cis isomer is heat-treated to conduct melt isomerization; and the like.

Preferred of these are the method in which an aqueous solution of the crude CHDA comprising a mixture of the trans isomer and the cis isomer is heat-treated to conduct isomerization and the method in which the crude CHDA comprising a mixture of the trans isomer and the cis isomer are heat-treated to conduct melt isomerization.

<Particle Diameter>

The particle diameter of the crude CHDA is not particularly limited as long as the crude CHDA can be introduced into and taken out of a reactor and can be stirred during the reaction according to need. However, the particle diameter thereof is generally 10 μm or larger, preferably 50 μm or larger, more preferably 100 μm or larger. Furthermore, the particle diameter thereof is generally 15 cm or smaller, preferably 10 cm or smaller, more preferably 5 cm or smaller. Smaller particle diameters are preferred from the standpoint of facilitating the volatilization of impurities.

It is generally preferred to use crude CHDA having a particle diameter of 300 μm or smaller, preferably 250 μm or smaller, especially 200 μm or smaller.

<Processes for Producing Powdery or Granular Crude CHDA>

Use may be made of powdery or granular crude CHDA produced by a known method or powdery or granular crude CHDA obtained by suitably pulverizing massive crude CHDA produced by a known method.

<Impurities in Starting Material>

The crude CHDA to be used as a starting material for isomerization reaction according to the invention preferably contain no impurity. However, the crude CHDA may contain substances which have a boiling point not higher than the isomerization reaction temperature and do not react with the crude CHDA, because such substances can be volatilized and removed during the isomerization reaction.

It is, however, preferred that the crude CHDA should contain water. This is because the presence of water in the crude CHDA is useful in removing organic impurities during the isomerization reaction, as will be described later in detail. The water content thereof is generally from 0.1 to 10% by weight.

Examples of the substances which have a boiling point not higher than the isomerization reaction temperature and do not react with the crude CHDA include the solvents used in steps for producing the crude CHDA, i.e., the solvent used for the hydrogenation reaction of TPA, the solvent used for the operation for returning an ester or metal salt to the carboxylic acid, etc. In particular, the crude CHDA obtained by the direct nucleus hydrogenation of TPA contain TPA, t-MCHA, c-MCHA, CHA, and the like as impurities in a large amount.

From the standpoint of production efficiency, the amount of impurities which may be contained in the reactant material is generally up to 30% by weight, preferably up to 15% by weight, based on the whole reactant material.

Even when such impurities are contained in the crude CHDA in a large amount, they can be volatilized and removed. However, from the standpoint of reducing the heating period, the impurity content of the crude CHDA to be subjected to purification is more preferably up to 10% by weight. When the isomerization according to the invention is conducted in an inert gas stream, it is possible to easily remove t-MCHA, which is difficult to remove by any of methods heretofore in use. Because of this, the crude CHDA may contain t-MCHA in an amount of from 1 to 6% by weight, especially from 1 to 4% by weight.

<Reactor>

The reactor to be used in the invention may be either a closed type reactor or an open type reactor. However, in the case of using an open type reactor, it should be one capable of being sealed with an inert gas so as to keep the reaction system in an inert atmosphere.

Although the reaction can be conducted batchwise or continuously, it is preferred to perform the reaction continuously from the standpoint of production efficiency. A reactor suitable for use in the continuous reaction in the invention is a gas flow type heater. Examples thereof include a rotary kiln, shaft stirring type baking machine, kneader type baking machine, fluidized-bed heating furnace, and the like.

<Method Characteristic of Flow Conditions>

One feature of the invention resides in that a reactant material is subjected to an isomerization reaction while being caused to flow.

Examples of apparatus for causing the reactant material to flow include an apparatus in which the main body (drum) rotates to move a powdery or granular material, an apparatus which forcedly move a powdery or granular material with a screw or the like, an apparatus in which a powdery or granular material is placed on an apron (holding plate) or the like and moved therewith, an apparatus in which a powdery or granular material is moved together with an air stream, and the like.

Preferred of those are the rotating drum type and screw conveyor type. More preferred is an apparatus having the function of inhibiting the crude CHDA from adhering to the apparatus or of separating the crude CHDA which has adhered.

The state of the reaction system during the isomerization reaction varies depending on the proportion of t-CHDA to the crude CHDA, the content of impurities, etc., and the stirring power required varies accordingly. Consequently, the preferred reactor varies.

The relationship between the proportion of t-CHDA and the state of the reaction system is roughly as follows.

(1) In the case where the proportion of t-CHDA to the crude CHDA is a half or more, the state of the reaction system is as follows. When the reactant material is held at a temperature in the range of from the melting point of c-CHDA to below the melting point of t-CHDA, then the reaction system comes into a state in which molten c-CHDA is adherent to the surface of the solid particles of t-CHDA. Namely, the crude CHDA retains a nearly solid state and are hence less apt to adhere to the inner wall and stirring part of the reactor. Consequently, a low stirring power suffices to cause the reactant material to flow. For example, use can be made of a rotary kiln, inverted-cone type ribbon stirring heater, inverted-cone type screw stirring heater, or the like.

(2) In the case where the proportion of t-CHDA to the crude CHDA is a half or less, the CHDA in the reaction system comes into a state in which t-CHDA suspends in molten c-CHDA, or the crude CHDA completely melts. Namely, the molten c-CHDA adheres to the inner wall and stirring part of the reactor. It may be thought that an inverted-cone type ribbon stirring heater, inverted-cone type screw stirring heater, or the like is effective. Virtually, however, the crude CHDA's adhere as a massive deposit to the ribbon or screw and, hence, the reaction product cannot be not only obtained as a powdery or granular material but also discharged. It is therefore necessary to stir the reaction system while removing the adherent CHDA.

Examples of an apparatus in which the adherent crude CHDA are removed simultaneously with stirring are as follows. In the case of a rotating drum, for example, it has a ball, rod, blade, or the like disposed therein so as to inhibit adhesion and accelerate pulverization. The drum is rotated to cause crude CHDA to flow and, simultaneously therewith, the ball, rod, or blade disposed therein rotates with the drum to thereby prevent the crude CHDA from adhering or remove and powder the adherent crude CHDA.

In the case of a screw conveyor, it has a small gap between the screw and the main body trough unlike the inverted-cone type screw stirring heater. Because of this, not only the crude CHDA flows when the screw rotates, but also a force is applied thereto in the direction opposite to the rotation due to contact with the trough. Thus, the crude CHDA can be prevented from adhering or the adherent crude CHDA can be removed and powdered. A twin-screw conveyor is more preferred because of interference between the screws.

<Methods for Introducing Crude CHDA to be Fed>

The state of the crude CHDA which is being fed to a reactor is not particularly limited. Use can be made of powdery or granular crude CHDA, a solvent-containing slurry of crude CHDA, a slurry comprising solid t-CHDA and molten c-CHDA heated at a temperature of from the melting point of c-CHDA to below the melting point of t-CHDA, a melt of crude CHDA heated at a temperature not lower than the melting point of t-CHDA, or the like.

Use of a melt of crude CHDA heated at a temperature not lower than the melting point of t-CHDA as a reactant material is preferred because the isomerization reaction time required before an equilibrium with the t-CHDA is reached can be reduced and because this reactant material is easy to handle since it is liquid. It should, however, be noted that this reactant material is introduced in an inert atmosphere because it may be oxidized and colored.

In the case where the reactant material is a powder, it is introduced into a reactor by a known method using a feeder, screw conveyor, or the like. When the reactant material is a granular material, it is introduced into a reactor by a known method using a belt conveyor, chain conveyor, or the like.

In the case where the reactant material is a slurry, it is introduced into a reactor by a known method using a slurry feeder or the like.

<Reaction Temperature>

In the invention, isomerization reaction is conducted at a temperature of from the melting point of c-CHDA to below the melting point of t-CHDA.

The term "melting points of c-CHDA and t-CHDA" as used in the invention means the melting points of c-CHDA and t-CHDA under the actual isomerization reaction conditions. Although it is known that the melting point of c-CHDA is 170-171° C. and the melting point of t-CHDA is 312-313° C., the melting points thereof vary depending on the kinds and amounts of impurities contained in the reactant material and on reaction conditions including pressure.

In case where the reaction temperature is lower than the melting point of c-CHDA, the rate of isomerization reaction is exceedingly low. Such low temperatures are hence practically unusable. The lower limit of the temperature for the thermal isomerization is generally not below the melting point of c-CHDA, preferably not below 190° C., more preferably not below 200° C., from the standpoint of improving the rate of isomerization reaction.

In case where the reaction temperature is not lower than the melting point of t-CHDA, isomerization cannot be conducted to a high t-isomer concentration because there is an equilibrium between the cis isomer and the trans isomer in the molten CHDA. It is therefore necessary to conduct isomerization at a temperature lower than below the melting point of t-CHDA. Namely, although the upper limit of the temperature for the thermal isomerization is not particularly limited as long as it is not higher than the melting point of t-CHDA, it is generally 310° C. or lower, preferably 300° C. or lower.

In this reaction, lower reaction temperatures result in prolonged isomerization reaction times. Higher reaction temperatures are advantageous because a shorter isomerization reaction time suffices, but result in an increased loss of the crude CHDA due to vaporization and volatilization. Consequently, an optimal reaction temperature is selected according to the t-isomer concentration of the starting material and the target t-isomer concentration. Methods for holding the reactant material at a temperature in the range of from the melting point of c-CHDA to below the melting point of t-CHDA are not particularly limited, and a holding temperature may be suitably selected.

The invention utilizes the difference in melting point between c-CHDA and t-CHDA, which are isomeric with each other, and an equilibrium in the isomerization reaction. One feature of the invention resides in that the temperature for the isomerization reaction is controlled.

When a mixture of c-CHDA and t-CHDA is held at a temperature in the range of from the melting point of c-CHDA to below the melting point of t-CHDA, then only the c-CHDA, which has a lower melting point, melts. As a result of the melting of c-CHDA, isomerization of c-CHDA to t-CHDA occurs so as to maintain an equilibrium state in which c-CHDA and t-CHDA are present in a given concentration ratio. The t-CHDA yielded by the isomerization precipitates in the c-CHDA because the temperature is lower than the melting point thereof. As a result of the precipitation, the concentration of t-CHDA decreases and, hence, the isomerization reaction of c-CHDA to t-CHDA in the molten c-CHDA is accelerated. Thus, high-purity t-CHDA as the target compound can be obtained. The reaction temperature according to the invention has advantages that impurities can be efficiently volatilized and reactor corrosion is inhibited.

Usually, the steps beginning with the heating of the reactant material and ending with the precipitation of t-CHDA in the molten c-CHDA are conducted at a temperature lower than the melting point of t-CHDA. In this method, when the reaction product after completion of the isomerization reaction is cooled to room temperature, t-CHDA is obtained as fusion-bonded acicular crystals. Consequently, the t-CHDA can be easily recovered from the reactor and the t-CHDA recovered can be easily pulverized. The reason for this may be that the t-CHDA in the reaction mixture does not melt and, hence, crystals of the crude CHDA which has undergone isomerization adhere to the t-CHDA present as a solid.

In contrast, in the case where isomerization is conducted with flowing, the reaction can be conducted advantageously even when the crude CHDA is heated to or above the melting point of t-CHDA and then held at a temperature of from the melting point of c-CHDA to below the melting point of t-CHDA.

When crude CHDA is heated to or above the melting point of t-CHDA, they completely melt and the c/t ratio in the melt rapidly reaches an equilibrium value (c/t is about (30-40)/(60-

70)). Because of this, the reaction time can be reduced when the crude CHDA as a starting material have a high cis isomer content. Furthermore, it is necessary to hold the reaction mixture at a temperature below the melting point of t-CHDA for a given time period at least at the outlet from the reactor, because the t-CHDA cannot be granulated when the temperature of the reaction mixture is equal to or higher than the melting point of t-CHDA.

Namely, the internal temperature of the reactor may be high as long as the temperature in an area around the outlet from the reactor is below the melting point of t-CHDA. For example, the temperature in an area around the inlet to the reactor may be not lower than the melting point of t-CHDA. Furthermore, it is, for example, possible to heat the crude CHDA to a temperature not lower than the melting point of t-CHDA with a melting tank or the like before isomerization reaction is conducted in a reactor. In the case of using a reactor in which the inlet and the outlet can have different temperatures, e.g., a rotary kiln, the temperature on the reactor inlet side may be elevated to or above the melting pint of t-CHDA.

<Reaction Pressure>

The reaction pressure may be any of a reduced pressure, ordinary pressure, and elevated pressure. However, the pressure is generally 1.3 kPa or higher, preferably 13 kPa or higher, more preferably 65 kPa or higher, and is generally 950 kPa or lower, preferably 700 kPa or lower, more preferably 400 kPa or lower. From the standpoint of ease of operation, ordinary pressure is most preferred.

<Reaction Time>

The reaction time varies depending on the particle diameter of the crude CHDA, reaction temperature, flow rate of an inert gas, degree of vacuum, target degree of isomerization, etc. However, from the standpoint of production efficiency, conditions are selected so that the target degree of isomerization is reached generally in 10 hours, preferably in 5 hours, more preferably in 1 hour. The reaction is generally conducted for 10 minutes or more. The term "reaction time" in the invention means the time period in which crude CHDA is heated or held at a temperature not lower then the melting point of c-CHDA. It is, however, preferred to hold crude CHDA at a temperature of from 180° C. to below the melting point of t-CHDA for 10 minutes or more.

<Reaction Atmosphere>

The reaction according to the invention is preferably conducted in an inert atmosphere. The term "inert atmosphere" as used herein means an atmosphere of a gas (inert gas) which does not substantially react with CHDA under the isomerization reaction conditions according to the invention. The inert gas in the invention has an oxygen content of 2% by volume or lower, preferably 1% by volume or lower, more preferably 0.5% by volume or lower.

The inert gas is not particularly limited. Examples thereof include carbon dioxide, nitrogen, argon, water vapor, hydrogen, mixtures of any desired gases of these, and the like. Preferred is carbon dioxide or nitrogen. Nitrogen is preferred for industrially conducting the reaction. The presence of water vapor is preferred for the reasons which will be described later.

In the case of using a closed type reactor, the atmosphere in the reactor is displaced by an inert gas. When an open type reactor is used, it is sealed with an inert gas or an inert gas is kept being passed therethrough.

The passing of an inert gas is more preferred because it is effective in efficiently volatilizing and removing organic impurities including the TPA remaining unreacted after the nucleus hydrogenation of TPA and by-products of the hydrogenation, such as t-MCHA, c-MCHA, and methylcyclohexane. In the case where an inert gas is passed, there are no particular limitations on the flow rate of the inert gas. The space velocity of the inert gas being passed is varied in order to reduce the amount of the inert gas to be used and the loss of the crude CHDA's and according to the concentration of impurities to be volatilized and removed. However, the space velocity thereof in the case of conducting thermal isomerization in an inert atmosphere is generally 1 hr$^{-1}$ or higher, preferably 5 hr$^{-1}$ or higher, more preferably 10 hr$^{-1}$ or higher, and is generally 2,000 hr$^{-1}$ or lower, preferably 1,500 hr$^{-1}$ or lower, more preferably 700 hr$^{-1}$ or lower.

By volatilizing and removing impurities by conducting thermal isomerization while passing an inert gas as described above, crude CHDA's can be obtained which have an organic-impurity content of 2% or lower, preferably 1.5% or lower, more preferably 1% or lower.

When water vapor is caused to be present in the reaction atmosphere, then the water vapor can be condensed together with impurities which have volatilized and the resultant slurry containing impurities can be discarded as it is. The T340 of the reaction product can be significantly improved. The presence of water is hence preferred.

In the case of using water vapor, the amount thereof in the atmosphere is generally 50 mg/L or larger, preferably 100 mg/L or larger, more preferably 200 mg/L or larger.

Examples of methods for attaining that water vapor amount in the invention include: (1) to use crude CHDA's containing water; (2) to use an inert gas containing water; (3) to directly introduce water vapor into the reactor; and the like. Preferred of these is the method in which crude CHDA's containing water are used, because this method attains a high contact efficiency.

In general, the crude CHDA to be used as a reactant material in the invention contains water because crude CHDA is taken out of aqueous solutions. However, when water is present, particles of the crude CHDA fuse to one another during storage of the crude CHDA to make the crude CHDA exceedingly difficult to handle. Namely, crude CHDA is generally stored after having been dried. It is, however, preferred that crude CHDA which has been dried be reacted after water is added thereto.

To use a reduced pressure is also preferred for removing impurities. In the case where impurities are volatilized by heating at a reduced pressure, a cooling zone may be disposed besides a heating zone in a vessel so that the impurities which have volatilized in the heating zone are condensed in the cooling zone and removed.

<Methods for Recovering Reaction Product>

Methods for recovering the reaction product are not particularly limited. Besides a method in which the reaction product is recovered after having been cooled to room temperature, examples of recovery methods include a method comprising precipitating t-CHDA in molten c-CHDA and then separating the precipitated t-CHDA from the molten c-CHDA.

Preferred embodiments of the production of t-CHDA include a method in which crude CHDA is continuously fed to a reactor and the t-CHDA precipitated is continuously separated and recovered from the molten c-CHDA. By this method, crystalline t-CHDA having a high purity can be continuously obtained.

<Reaction Product to be Obtained>

According to the invention, c-CHDA can be efficiently isomerized into t-CHDA in the manner described above, whereby t-CHDA having a t/(c+t) of 0.8 or higher, preferably 0.9 or higher, more preferably 0.95 or higher, can be obtained.

When isomerization reaction is conducted in a stream of an inert gas, CHDA having an impurity content of 1% by weight or lower can be obtained.

Use of the CHDA obtained by the invention, which has a high t-CHDA content, can yield resins and fibers excellent in heat resistance, weatherability, physical strength, etc.

When crude CHDA in a powdery or granular state is heat-treated and isomerized while maintaining the powdery or granular state, then the crude CHDA charged into the reactor retains a solid state throughout the reaction time. As a result, powdery or granular CHDA having almost the same particle diameter as that before the reaction is formed.

Furthermore, when the thermal isomerization is conducted while causing the crude CHDA to flow, the t-CHDA obtained through the reactor outlet is in the form of a powdery or granular material generally having a size of several centimeters or smaller.

<High-Quality t-CHDA>

According to the process for t-CHDA production described above, high-quality t-CHDA of the invention which satisfies the following (a) and (b) can be obtained:
(a) a t-isomer content is 90% or higher; and
(b) a transmittance at 340 nm is 85% or higher in an aqueous alkali solution.

This high-quality t-CHDA, which has a t-isomer content of 90% or higher, gives a polymer having excellent thermal properties.

t-Isomer contents can be determined by liquid chromatography; "%" here means "% by weight".

The high-quality t-CHDA has a light transmittance of 85% or higher as measured at a wavelength of 340 nm. When the light transmittance thereof is lower than 85%, there are cases where polymeric compounds produced from this CHDA have a reduced light transmittance. Namely, the polymers obtained may have poor transparency.

Light transmittance at a wavelength of 340 nm can be determined, for example, by examining a solution prepared by dissolving 1 g of a sample in 10 mL of 2 N KOH solution with a spectrophotometer using a quartz cell having a thickness of 1 cm.

High-quality t-CHDA which further satisfies the following requirements can be obtained:
(c) a total content of alkali metals and alkaline earth metals is 20 ppm or lower; and
(d) an acid radical content is 25 ppm or lower.

The content of alkali metals and alkaline earth metals is preferably 15 ppm or lower, more preferably 10 ppm or lower. According to the process of the invention, high-quality t-CHDA substantially free from alkali metals and alkaline earth metals is obtained. In case where the content of alkali metals and alkaline earth metals exceeds 20 ppm, there is a possibility that the CHDA might be present in the form of a carboxylic acid metal salt. This metal salt may influence reaction behaviors and the electrical properties of polymers obtained therefrom. There also is a possibility that metal dissolution from such polymers might occur to foul machines or apparatus, etc.

The term "alkali metals" as used herein means sodium, potassium, and the like, while the alkaline earth metals represent magnesium, calcium, and the like. The content of such metals can be determined, e.g., by emission spectroscopy.

On the other hand, in case where the content of acid radicals exceeds 25 ppm, acidity increases and this may cause corrosion of apparatus, etc. The acid radical content is preferably 20 ppm or lower, more preferably 10 ppm or lower.

The term "acid radicals" as used herein means ones which come when a TPA ester or TPA metal salt which has been hydrogenated is treated by acid precipitation with sulfuric acid, hydrochloric acid, or the like. In the case of sulfuric acid, the acid radicals represent metal salts of sulfuric acid, sulfate ions, and sulfur besides sulfuric acid. In the case of hydrochloric acid, the acid radicals represent metal salts of hydrochloric acid, chlorine ions, and the like besides hydrochloric acid. The kinds of the ions of such acid radicals can be easily determined by, e.g., ion chromatography, while the total sulfur or total chlorine content can be easily determined by, e.g., emission spectrometry.

EXAMPLES

The invention will be explained below in detail by reference to Examples, but the invention should not be construed as being limited to these Examples.

Example 1

Into an autoclave having a capacity of 70 mL were introduced 0.2 g of crude CHDA consisting of 92.6% by weight c-CHDA and 7.4% by weight t-CHDA. The atmosphere in the autoclave was displaced by nitrogen. The autoclave was held at 230° C. for 1 hour without stirring the crude CHDA. Thereafter, the autoclave was cooled to room temperature. As a result, a solid in the form of fusion-bonded acicular crystals was obtained. The results of analysis of this solid by liquid chromatography (hereinafter referred to as LC) are shown in Table 1.

Example 2

The same procedure as in Example 1 was conducted, except that the holding period was changed to 3 hours. As a result, a solid in the form of fusion-bonded acicular crystals was obtained. The results of analysis of this solid by LC are shown in Table 1.

Example 3

The same procedure as in Example 1 was conducted, except that the holding temperature was changed to 250° C. As a result, a solid in the form of fusion-bonded acicular crystals was obtained. The results of analysis of this solid by LC are shown in Table 1.

Example 4

The same procedure as in Example 1 was conducted, except that the holding temperature was changed to 270° C. As a result, a solid in the form of fusion-bonded acicular crystals was obtained. The results of analysis of this solid by LC are shown in Table 1.

Example 5

One gram of crude CHDA consisting of 92.6% by weight c-CHDA and 7.4% by weight t-CHDA were introduced into a reaction tube having a length of 30 cm and an inner diameter of 20 mm and equipped with gas inlet and gas outlet cocks in an upper part thereof. An argon introduction tube equipped with a bubbler was connected to the inlet of the reaction tube, and displacement by argon was sufficiently conducted.

Thereafter, the outlet cock was closed and argon was bubbled with the bubbler to seal the reaction tube with argon. This reaction tube was held at 290° C. for 1 hour and then cooled to room temperature. As a result, a solid in the form of fusion-bonded acicular crystals was obtained, which had been formed on the bottom of the reaction tube. The results of analysis of this solid by LC are shown in Table 1.

Example 6

The same procedure as in Example 5 was conducted, except that the reaction tube was held at 330° C. for 0.5 hours and then held at 250° C. for 1 hour. As a result, a hard massive solid was obtained. The results of analysis of this solid by LC are shown in Table 1.

Comparative Example 1

The same procedure as in Example 5 was conducted, except that the reaction was conducted at a temperature of 310° C. to completely melt the reaction mixture and the mixture was then cooled to 180° C. over about 4 minutes. As a result, a hard massive solid was obtained. The results of analysis of this solid by LC are shown in Table 1.

Comparative Example 2

The same procedure as in Example 5 was conducted, except that the reaction was conducted at a temperature of 330° C. and the reaction mixture was cooled to 180° C. over about 4 minutes and 40 seconds. As a result, a hard massive solid was obtained. The results of analysis of this solid by LC are shown in Table 1.

Comparative Example 3

The same procedure as in Comparative Example 2 was conducted, except that the reaction time was changed to 3 hours. As a result, a hard massive solid was obtained. The results of analysis of this solid by LC are shown in Table 1.

Example 7

An aqueous solution containing 20% by weight TPA and 2% by weight 5%-Pd/C (manufactured by N.E. Chemcat) was introduced into an induction stirring type autoclave made of stainless steel. After nitrogen displacement, the contents were heated at a hydrogen pressure of 1 MPa and held for 2 hours at 150° C. and a hydrogen pressure of 5 MPa.

After completion of the reaction, the liquid reaction mixture was filtered through a sinter filter at 150° C. to remove the catalyst. The filtrate was cooled to 80° C., and the crude CHDA precipitated was taken out by filtration. The crude CHDA was analyzed by LC. As a result, the reaction product was found to comprise 10.6% by weight c-CHDA, 78.4% by weight t-CHDA, 0.3% by weight TPA, 0.1% by weight CHA, 1.3% by weight 4-methylcyclohexanecarboxylic acid (hereinafter referred to as MCHA), and 9.3% by weight water.

Five grams of the crude CHDA thus obtained were charged into a vertical glass reactor having an inner diameter of 15 mm and equipped at the outlet with a trap cooled with 5° C. water. Nitrogen was caused to flow downward at a space velocity of 276 hr$^{-1}$, and the crude CHDA was held at 200° C. for 1 hour and then cooled to room temperature. As a result, a solid in the form of fusion-bonded acicular crystals was obtained in the reaction tube. The results of analysis of this solid by LC are shown in Table 2.

Example 8

Reaction was conducted in the same manner as in Example 7, except that the holding period was changed to 3 hours. The results are shown in Table 2.

Example 9

Reaction was conducted in the same manner as in Example 7, except that the reaction temperature was changed to 250° C. The results are shown in Table 2.

TABLE 1

| | Reaction temperature (° C.) | Reaction time (hr) | Composition after reaction (wt %) | | State of reaction product |
|---|---|---|---|---|---|
| | | | c-CHDA | t-CHDA | |
| Example 1 | 230 | 1 | 20.8 | 79.2 | fusion-bonded acicular crystals |
| Example 2 | 230 | 3 | 6.6 | 93.4 | fusion-bonded acicular crystals |
| Example 3 | 250 | 1 | 13.5 | 86.5 | fusion-bonded acicular crystals |
| Example 4 | 270 | 1 | 9.5 | 90.5 | fusion-bonded acicular crystals |
| Example 5 | 290 | 1 | 3.1 | 96.9 | fusion-bonded acicular crystals |
| Example 6 | 330 | 0.5 | 5.4 | 94.6 | hard massive state |
| | 250 | 1 | | | hard massive state |
| Comparative Example 1 | 310 | 1 | 22.7 | 77.3 | hard massive state |
| Comparative Example 2 | 330 | 1 | 19.7 | 80.3 | hard massive state |
| Comparative Example 3 | 330 | 3 | 29.6 | 70.4 | hard massive state |

TABLE 2

| | Space velocity (hr⁻¹) | Temperature (°C.) | Period (hr) | Residue (g) | Composition of residue (wt %) | | | | |
|---|---|---|---|---|---|---|---|---|---|
| | | | | | c-CHDA | t-CHDA | TPA | CHA | MCHA |
| Example 7 | 276 | 200 | 1 | 4.43 | 7.4 | 91.5 | 0.2 | 0 | 0.9 |
| Example 8 | 276 | 200 | 3 | 4.40 | 3.8 | 95.4 | 0.1 | 0 | 0.7 |
| Example 9 | 276 | 250 | 1 | 4.21 | 1.8 | 97.8 | 0.1 | 0 | 0.3 |

Example 10

Crude CHDA having a t/(c+t) of 0.55 (average particle diameter, about 0.1 mm) was prepared by adding t-CHDA to crude CHDA obtained by the nucleus hydrogenation of TPA. Two grams of the crude CHDA thus obtained were introduced into a reaction tube having a length of 30 cm and an inner diameter of 20 mm and equipped with gas inlet and gas outlet cocks in an upper part thereof. An argon introduction tube was connected to the inlet of the reaction tube, and the atmosphere in the reactor was sufficiently displaced by argon. This reaction tube was set in an electric furnace heated at 250° C. and held therein in this state for 2 hours. As a result, the crude CHDA charged into the reactor retained a solid state throughout the reaction time, and powdery or granular CHDA having almost the same particle diameter as that before the reaction were obtained. The CHDA thus obtained was analyzed by LC. As a result, the t/(c+t) was found to be 0.963.

Reference Example 1

Reaction was conducted in the same manner as in Example 10, except that powdery or granular crude CHDA having a t/(c+t) of 0.455 (average particle diameter, about 0.1 mm) was used. In an initial stage of the reaction, a CHDA liquefied. After completion of the reaction, the CHDA was allowed to cool naturally to room temperature. As a result, the CHDA in the reactor became one mass, which was adherent to the wall of the reactor and difficult to take out of the reactor. The CHDA was analyzed by LC and, as a result, was found to have a t/(c+t) of 0.955.

Example 11

Ten grams of crude CHDA having a t/(c+t) of 0.376 were introduced together with 50 g of water into a 200-mL autoclave made of stainless steel. The atmosphere in the autoclave was sufficiently displaced by nitrogen, and the contents were heated at 250° C. for 1 hour with induction stirring. After completion of the reaction, the liquid reaction mixture was cooled to room temperature, and the crude CHDA precipitated was recovered. These crude CHDA was in a powdery or granular state. Analysis by LC revealed that this reaction product was powdery or granular crude CHDA having a t/(c+t) of 0.618 (average particle diameter, about 0.1 mm).

Two grams of the crude CHDA thus obtained were subjected to isomerization reaction in the same manner as in Example 10. The CHDA retained a solid state throughout the reaction time, and powdery or granular CHDA having almost the same particle diameter as that before the reaction were obtained. The CHDA thus obtained was analyzed by LC. As a result, the reaction product was found to be CHDA having a t/(c+t) of 0.956.

Example 12

Two grams of crude CHDA having a t/(c+t) of 0.376 were reacted at 330° C. for 1 hour in the same manner as in Example 10. During the reaction, the crude CHDA was liquid. The liquid crude CHDA was rapidly poured into a stainless-steel vessel having a flat bottom. The crude CHDA solidified could be easily separated from the stainless-steel vessel. Analysis by LC revealed that this reaction produce was crude CHDA having a t/(c+t) of 0.638.

The crude CHDA separated from the stainless-steel vessel was pulverized into a powdery or granular state having a particle diameter of about 0.1 mm. Thereafter, 2 g of the crude CHDA were subjected to isomerization reaction in the same manner as in Example 10. The CHDA retained a solid state throughout the reaction time, and powdery or granular CHDA having almost the same particle diameter as that before the reaction were obtained. Analysis by LC revealed that this reaction product was CHDA having a t/(c+t) of 0.965.

Reference Example 2

Two grams of crude CHDA having a t/(c+t) of 0.45 were subjected to isomerization reaction in the same manner as in Example 10, except that the crude CHDA was held at 330° C. for 1 hour. The CHDA was liquid throughout the reaction. After completion of the reaction, the CHDA was allowed to cool naturally to room temperature. The CHDA in the reactor became one mass, which was adherent to the wall of the reactor and difficult to take out of the reactor. Analysis by LC revealed that this reaction product was CHDA having a t/(c+t) of 0.793.

Example 13

An aqueous solution containing 20% by weight TPA and 2% by weight 5%-Pd/C (manufactured by N.E. Chemcat) was introduced into an induction stirring type autoclave made of stainless steel. After nitrogen displacement, the contents were heated at a hydrogen pressure of 1 MPa and held for 2 hours at 150° C. and a hydrogen pressure of 5 MPa. After completion of the reaction, the liquid reaction mixture was filtered through a sinter filter at 150° C. to remove the catalyst. Analysis by LC revealed that the conversion of the TPA was 99.5% by mole, the yield of 4-methylcyclohexanecarboxylic acid (hereinafter referred to as MCHA) was 3.1% by mole, the yield of cyclohexanecarboxylic acid (hereinafter referred to as CHA) was 0.22% by mole, and the yield of CHDA was 96.2% by mole. It was further found that the crude CHDA had a t/(c+t) of 0.35.

This aqueous solution was further introduced into the induction stirring type autoclave made of stainless steel, and reacted at 250° C. for 2 hours in a nitrogen atmosphere. As a result, an aqueous solution of crude CHDA having a t/(c+t) of 0.618 was obtained. This liquid reaction mixture was cooled to room temperature, and the precipitate was taken out by filtrating and analyzed by LC. As a result, the precipitate was found to comprise 4.8% by weight water, 1.6% by weight MCHA, 0.1% by weight CHA, 0.5% by weight TPA, and 93.0% by weight CHDA, and the crude CHDA was found to have a t/(c+t) of 0.671.

Five grams of the crude CHDA thus obtained were pulverized into a powdery or granular state having a particle diameter of about 0.1 mm, and then introduced into a vertical down-flow type glass reactor having an inner diameter of 22 mm. Argon was caused to flow downward at 276 $hr^{-1}$ to react the crude CHDA's at 250° C. for 2 hours. As a result, the crude CHDA introduced retained a solid state throughout the reaction time, and powdery or granular CHDA having almost the same particle diameter as that before the reaction were obtained.

As a result, the reaction product recovered amounted to 4.43 g. Analysis by LC revealed that the reaction product comprised 0.4 wt % MCHA, 0.2 wt % TPA, and 99.4 wt % CHDA, and the CHDA had a t/(c+t) of 0.971.

Example 14

A crude CHDA powder consisting of 45.0% c-CHDA and 55.0% t-CHDA was continuously introduced in an amount of 6.6 kg into a rotary kiln (length, 4 m; inner diameter, 200 mm; radial furnace manufactured by Akami Seisaku-sho) having a built-in pulverizer (beater) over 28 minutes in a nitrogen atmosphere. The powder was treated under the conditions of a furnace temperature of 250° C. and a residence time of about 8 minutes. The CHDA's thus isomerized were continuously discharged in a powder state from the rotary kiln. The composition thereof had a t-CHDA content of 96%.

Reference Example 3

Into a 2-liter flask equipped with a Three-One Motor having a stirring blade were introduced 500 g of crude CHDA (t-isomer content, 35%). After sufficient nitrogen displacement, the contents were heated with stirring to 250° C. on an oil bath in a stream of a small amount of nitrogen. At about 20 minutes after initiation of the heating, the stirring became difficult and was hence stopped. After the internal temperature reached 250° C., this temperature was maintained for 1 hour.

After the treatment, the reaction product was cooled and analyzed for CHDA content. As a result, the t-isomer content was found to be 95%. However, in this stirring method, the CHDA adherent to the stirring blade only rotated together with the stirring blade and could not be separated therefrom. Consequently, the CHDA had consolidated into one mass and was difficult to take out.

Reference Example 4

Ribocone (Type RM-10D; effective capacity, 13.2 L), manufactured by Okawara MFG., was heated to 120° C. Thereinto were introduced 5.2 kg of crude CHDA (c-CHDA, 86.0%; t-CHDA, 14.0%) at atmospheric pressure. The crude CHDA was treated for 90 minutes with stirring at a ribbon revolution speed of about 100 rpm. Thereafter, nitrogen displacement was conducted. The contents were subsequently heated and treated at 190° C. for 60 minutes, and further heated and treated at 270° C. for 120 minutes.

After the treatment, an attempt was made to discharge from a lower part of the reactor. However, the CHDA could not be discharge through the discharge opening.

The ribbon was taken out of the can and the CHDA were recovered and analyzed. As a result, the t-isomer content was found to be 97.6%. However, a residue of the CHDA remained adherent sporadically to the can cone part. The CHDA adherent to the ribbon part only rotated together with the ribbon and could not be separated therefrom. The CHDA hence was present as a mass.

Example 15

An aqueous solution containing 20% by weight TPA and 2% by weight 5%-Pd/C (manufactured by N.E. Chemcat) was introduced into an induction stirring type autoclave made of stainless steel. After nitrogen displacement, the contents were heated at a hydrogen pressure of 1 MPa and held for 2 hours at 150° C. and a hydrogen pressure of 5 MPa.

After completion of the reaction, the liquid reaction mixture was filtered through a sinter filter at 150° C. to remove the catalyst. The filtrate was cooled to 80° C., and the crude CHDA precipitated was taken out by filtration. The crude CHDA was analyzed by LC. As a result, the reaction product was found to comprise 10.6% by weight c-CHDA, 78.4% by weight t-CHDA, 0.3% by weight TPA, 0.1% by weight CHA, 1.3% by weight MCHA, and 9.3% by weight water.

Five grams of the CHDA thus obtained were charged into a vertical glass reactor having an inner diameter of 15 mm and equipped at the outlet with a trap cooled with 5° C. water. Nitrogen was caused to flow downward at a space velocity of 276 $hr^{-1}$, and the crude CHDA was held at 250° C. for 1 hour and then cooled to room temperature. As a result, a solid in the form of fusion-bonded acicular crystals was obtained in the reaction tube. The solid obtained was analyzed by LC. As a result, the solid was found to comprise 1.8% by weight c-CHDA, 97.8% by weight t-CHDA, 0.1% by weight TPA, 0% CHA, and 0.3 wt % MCHA.

Example 16

Twenty parts by weight of TPA was suspended in 80 parts by weight of water. Thereto was added 2 parts by weight of 5%-Pd/C (manufactured by N.E. Chemcat Corp.). This mixture was introduced into an induction stirring type autoclave made of stainless steel. The air in the vessel was displaced by nitrogen. Subsequently, the contents were heated to 150° C. while introducing hydrogen at a hydrogen pressure of 1 MPa. The hydrogen pressure was regulated to 5 MPa and the mixture was reacted for 2 hours under these conditions. The reaction mixture was filtered through a sinter filter at 150° C. to remove the catalyst. Thereafter, the liquid reaction mixture was cooled to 80° C., and the crude CHDA precipitated was taken out by filtration. These crude CHDA had a particle diameter smaller than 120 μm and had a composition comprising 89.0% by weight CHDA, 0.3% by weight TPA, 0.1% by weight CHA, 0.1% by weight c-MCHA, 1.2% by weight t-MCHA, and 9.3% by weight water.

Five grams of the crude CHDA obtained were charged into a vertical glass reactor having an inner diameter of 15 mm and equipped at the outlet with a trap cooled with 5° C. water. The crude CHDA was heated at 250° C. for 1 hour while causing nitrogen to flow downward at a space velocity of 276 $hr^{-1}$. Thereafter, the CHDA remaining in the reactor (hereinafter referred to as "purified CHDA") was analyzed. The results are shown in Table 3.

Example 17

Purified CHDA was obtained through heating in the same manner as in Example 16, except that the heating period of 1 hour in Example 16 was changed to 3 hours. The results of analysis are shown in Table 3.

Example 18

Purified CHDA was obtained through heating in the same manner as in Example 16, except that the heating temperature of 250° C. in Example 16 was changed to 200° C. The results of analysis are shown in Table 3.

Example 19

Crude CHDA obtained in the same manner as in Example 16 was dried at 50° C. and 5 mmHg for 2 hours. These crude CHDA had a particle diameter smaller than 120 μm and had a composition comprising 98.0% by weight CHDA, 0.3% by weight TPA, 0.1% by weight CHA, 0.1% by weight c-MCHA, and 1.5% by weight t-MCHA.

These crude CHDA was heated under the same conditions as in Example 16 to obtain purified CHDA. The results of analysis are shown in Table 3.

Example 20

Purified CHDA was obtained through heating under the same conditions as in Example 19, except that the heating temperature of 250° C. in Example 19 was changed to 230° C. The results of analysis are shown in Table 3.

Example 21

Purified CHDA was obtained through heating under the same conditions as in Example 20, except that use was made of crude CHDA (particle diameter, smaller than 44 μm) obtained by pulverizing the dried crude CHDA obtained in Example 19 with an agate mortar and then passing the pulverized particles through a 350-mesh sieve, and that the space velocity of 276 hr$^{-1}$ in Example 20 was changed to a space velocity of 36 hr$^{-1}$. The results of analysis are shown in Table 3.

Example 22

The dried crude CHDA obtained in Example 19 was charged into a vertical glass reactor having an inner diameter of 15 mm. The space between the top of the reactor and the crude CHDA was filled with glass beads having a diameter of 2 mm. The contents were heated at 250° C. for 1 hour while generating water vapor by supplying water at 0.05 mL/min to the glass bead layer heated at 250° C. Thereafter, the purified CHDA remaining in the reactor were analyzed. The results are shown in Table 3.

TABLE 3

| | Purified CHDA (g) | Composition of purified CHDA | | | | |
|---|---|---|---|---|---|---|
| | | CHDA (wt %) | TPA (wt %) | CHA (wt %) | c-MCHA (wt %) | t-MCHA (wt %) |
| Example 16 | 4.52 | 99.6 | 0.1 | 0 | 0 | 0.3 |
| Example 17 | 3.97 | 99.7 | 0.1 | 0 | 0 | 0.2 |
| Example 18 | 4.43 | 98.9 | 0.2 | 0 | 0 | 0.9 |
| Example 19 | 4.65 | 99.6 | 0.1 | 0 | 0 | 0.3 |
| Example 20 | 4.96 | 99.1 | 0.3 | 0 | 0 | 0.6 |
| Example 21 | 4.43 | 99.5 | 0.1 | 0 | 0 | 0.4 |
| Example 22 | 4.57 | 99.5 | 0.1 | 0 | 0 | 0.4 |

Example 23

Into a 130-L autoclave made of SUS316 were introduced 10 kg of TPA, 90 kg of water, and 2 kg of a 5%-Pd/C catalyst (containing 50% water). Thereafter, hydrogenation reaction was conducted with stirring at 150° C. and 5 MPa for 1 hour until hydrogen consumption ended. The liquid reaction mixture obtained was cooled to 110° C. Thereafter, the catalyst was separated by filtration, and the filtrate was further cooled to 25° C. and allowed to stand overnight to crystallize CHDA. This mixture was filtered with a centrifugal separator, and the cake obtained was dried at 110° C. and 5 mmHg for 2 hours to obtain CHDA (t-isomer, 31.6%). In a 0.5-L flask made of glass were placed 100 g of the CHDA obtained. After evacuation and displacement with nitrogen, heat treatment was conducted at 250° C. for 1 hour while passing the gas. The t-CHDA obtained was analyzed for transmittance at 340 nm (hereinafter referred to as T340) and for sulfur, chlorine, and sodium. The results of the analysis are shown in Table 4.

T340 was determined by examining a solution prepared by dissolving 1 g of a sample in 10 mL of 2 N KOH solution using a spectrophotometer (Hitachi Ratio Beam Spectrophotometer Type U-1100, manufactured by Hitachi Ltd.) and a quartz cell having a thickness of 1 cm. With respect to sulfur, chlorine, and sodium, the total sulfur content, total chlorine content, and total sodium content were determined by measuring the amount of sulfate ions or compounds containing the same, amount of chlorine ions or compounds containing the same, and amount of sodium ions or compounds containing the same, respectively, by emission spectroscopy.

Comparative Example 4 t-CHDA manufactured by Tokyo Kasei Co., Ltd. was analyzed in the same manner as in Example 23. The results are shown in Table 4.

Comparative Example 5 t-CHDA manufactured by Aldrich Inc. was analyzed in the same manner as in Example 23. The results are shown in Table 4.

Comparative Example 6

Into a beaker made of glass were introduced 40 g of CHDA (t-isomer concentration, 26.3%) manufactured by Eastman Chemical and 60 g of water. The contents were heated to 80° C. with stirring. Thereafter, this mixture was filtered at 80° C., washed with 100 mL of 80° C. water, and dried at 110° C. and 5 mmHg for 2 hours to obtain t-CHDA. This t-CHDA was analyzed in the same manner as in Example 23. The results are shown in Table 4.

Comparative Example 7

Into an autoclave made of stainless steel were introduced 40 g of CHDA (t-isomer, 26.3%) manufactured by Eastman Chemical and 60 g of water. The contents were heated in a nitrogen atmosphere at 245-250° C. for 2 hours. Thereafter, the reaction mixture was cooled to 80° C., filtered at 70° C., washed with 100 mL of 80° C. water, and dried at 110° C. and 5 mmHg for 2 hours to obtain t-CHDA. This t-CHDA was analyzed in the same manner as in Example 23. The results are shown in Table 4.

TABLE 4

|  | t-CHDA (%) | T340 (%) | Total sulfur (ppm) | Total chlorine (ppm) | Total sodium (ppm) |
|---|---|---|---|---|---|
| Example 23 | 94.9 | 92.9 | <5 | <5 | <0.03 |
| Comparative Example 4 | 98.0 | 80.9 | <5 | 33 | 5 |
| Comparative Example 5 | 97.8 | 78.5 | <5 | 38 | 5.6 |
| Comparative Example 6 | 96.8 | 81.1 | <5 | <5 | 9 |
| Comparative Example 7 | 99.2 | 75.5 | <5 | <5 | 1 |

Example 24

Ten grams of CHDA including 37% by weight c-CHDA were introduced into a four-necked flask equipped with a gas introduction tube, cooling pipe, and stirrer. The flask was evacuated with a vacuum pump and the internal pressure was then returned to ordinary pressure with nitrogen (makeup gas) containing 2 ppm oxygen. This operation was repeatedly conducted five times to displace the atmosphere in the flask by the makeup gas. The contents were heated to 250° C. and heat-treated for 1 hour with stirring while introducing the makeup gas through the gas introduction tube at 1 L/hr. After cooling to room temperature, the CHDA present in the flask was wholly recovered and analyzed by liquid chromatography.

Example 25

Reaction was conducted in the same manner as in Example 24, except that the gas passed during the isomerization reaction of the CHDA was nitrogen which contained 15 mg/L water vapor and had been prepared beforehand by bubbling nitrogen into room-temperature (25° C.) water to saturate the nitrogen with water vapor. The results are shown in Table 5.

Example 26

Reaction was conducted in the same manner as in Example 24, except that the gas passed during the isomerization reaction of the CHDA was nitrogen which contained 232 mg/L water vapor and had been prepared by introducing water vapor at 10 g/hr into the flask simultaneously with nitrogen introduction. The results are shown in Table 5.

TABLE 5

|  | Water vapor concentration (mg/L) | t-CHDA (%) | T340 (%) |
|---|---|---|---|
| Example 24 | 0 | 95.9 | 92.1 |
| Example 25 | 15 | 94.9 | 92.9 |
| Example 26 | 232 | 94.9 | 95.9 |

Reference Example 5

A test piece made of SUS-316 and having a known weight was immersed in CHDA (t-isomer, 34.1%; sulfur<5 ppm; chlorine<5 ppm; sodium<0.03 ppm). This test piece was heat-treated at 250° C. for 1 hour in a nitrogen atmosphere of 1 MPa. After the treatment, the test piece was washed. The surface area and weight of the test piece were measured before and after the treatment to calculate the rate of corrosion (mm/year). As a result, the corrosion rate was found to be 0.04 mm/year.

Reference Example 6

CHDA (t-isomer, 26.3%; sulfur, 9.2 ppm; chlorine<5 ppm; sodium>29 ppm) manufactured by Eastman Chemical were evaluated in the same manner as in Reference Example 5. As a result, the corrosion rate was found to be 0.23 mm/year.

Reference Example 7

The same evaluation as in Reference Example 5 was conducted, except that the 1-hour heat treatment was performed at 330° C. As a result, the corrosion rate was found to be 4.52 mm/year.

While the invention has been described in detail and with reference to specific embodiments thereof, it will be apparent to one skilled in the art that various changes and modifications can be made therein without departing from the spirit and scope thereof.

This application is based on a Japanese patent application filed on Oct. 26, 2001 (Application No. 2001-329101), Japanese patent application filed on Dec. 4, 2001 (Application No. 2001-369959), Japanese patent application filed on Apr. 16, 2002 (Application No. 2002-113047), and Japanese patent application filed on May 23, 2002 (Application No. 2002-149302), the contents thereof being herein incorporated by reference.

INDUSTRIAL APPLICABILITY

According to the invention, the isomerization of c-CHDA to t-CHDA can be efficiently conducted. When the CHDA obtained by the invention, which has a high t-CHDA purity, is used, resins or fibers excellent in heat resistance, weatherability, physical strength, etc. can be produced.

The high-quality t-CHDA of the invention has the following excellent properties. It has a low acid radical content and, hence, does not corrode polymerization vessels. It has a low content of alkalis and alkaline earth metals and, hence, is inhibited from changing in reaction behavior during polymerization reaction. The resultant polymer can have stabilized electrical properties. Furthermore, the t-CHDA has a high T340 and is hence highly transparent.

The invention claimed is:

1. A trans-1,4-cyclohexanedicarboxylic acid composition comprising trans-1,4-cyclohexanedicarboxylic acid in an amount of 90% or higher, wherein
   a transmittance of the trans-1,4-cyclohexanedicarboxylic acid composition at 340 nm is 85% or higher when the transmittance is determined by examining an alkali solution, which is prepared by dissolving 1 g of the trans-1,4-cyclohexanedicarboxylic acid composition in 10 mL of 2N KOH solution, with a spectrophotometer using a quartz cell having a thickness of 1 cm; and
   the trans-1,4-cyclohexanedicarboxylic acid composition further comprises trans-4-methylcyclohexanecarboxylic acid in an amount ranging from 0.2 to 0.9 wt %.

2. The trans-1,4-cyclohexanedicarboxylic acid composition according to claim 1, further comprising at least one of
   a total content of alkali metals and alkaline earth metals of 20 ppm or lower; and
   an acid radical content of 25 ppm or lower.

3. The trans-1,4-cyclohexanedicarboxylic acid composition according to claim 2, wherein the acid radical content is a total content of sulfur and chlorine as determined by an emission spectrometry.

4. The trans-1,4-cyclohexanedicarboxylic acid composition according to claim 1, further comprising cis-1,4-cyclohexanedicarboxylic acid, wherein a weight ratio of trans-1,4-cyclohexanedicarboxylic acid to a sum of trans-1,4-cyclohexanedicarboxylic acid and cis-1,4-cyclohexanedicarboxylic acid is 0.8 or higher.

5. The trans-1,4-cyclohexanedicarboxylic acid composition according to claim 1, wherein the trans-1,4-cyclohexanedicarboxylic acid composition further comprises terephthalic acid in an amount of 0.3 wt % or less.

6. The trans-1,4-cyclohexanedicarboxylic acid composition according to claim 1, wherein the transmittance of the trans-1,4-cyclohexanedicarboxylic acid composition at 340 nm is 92.9% or higher.

7. The trans-1,4-cyclohexanedicarboxylic acid composition according to claim 1, wherein the trans-1,4-cyclohexanedicarboxylic acid is in the form of acicular crystals or a mass.

8. The trans-1,4-cyclohexanedicarboxylic acid composition according to claim 1, wherein the trans-1,4-cyclohexanedicarboxylic acid is in the form of acicular crystals.

* * * * *